United States Patent [19]

Fuisz

[11] Patent Number: 5,096,492
[45] Date of Patent: Mar. 17, 1992

[54] DISPERSED SYSTEMS AND METHOD OF MANUFACTURE

[75] Inventor: Richard C. Fuisz, Washington, D.C.

[73] Assignee: Fuisz Technologies Ltd., Chantilly, Va.

[21] Appl. No.: 602,485

[22] Filed: Oct. 24, 1990

Related U.S. Application Data

[60] Division of Ser. No. 283,742, Dec. 13, 1988, Pat. No. 5,011,532, which is a continuation-in-part of Ser. No. 169,838, Mar. 18, 1988, Pat. No. 4,855,326, which is a continuation-in-part of Ser. No. 40,371, Apr. 20, 1987, abandoned.

[51] Int. Cl.$^5$ ............................................. C09D 105/00
[52] U.S. Cl. .................................... 106/215; 426/658; 426/660
[58] Field of Search ................ 426/660, 658; 106/162, 106/215, 217

[56] References Cited

U.S. PATENT DOCUMENTS 4,873,085  10/1989  Fuisz .................................... 514/777
5,011,532  4/1991   Fuisz .................................... 106/215

OTHER PUBLICATIONS

Hawley, *The Condensed Chemical Dictionary*, van Nostrand Reinhold, NY, 1974, pp. 421, 449.

*Primary Examiner*—Theodore Morris
*Assistant Examiner*—David M. Brunsman
*Attorney, Agent, or Firm*—Hoffmann & Baron

[57] ABSTRACT

Oleaginous substances such as vegetable oil, baby oil, olive oil, margarine, lanolin, cocoa butter and the like have their affinity for water altered by mixing the oleaginous substance with sugar and melt spinning the mixture in a cotton candy spinning machine or the equivalent. As so modified the product disperses autogenously in water forming a colloidal or colloidal-like dispersion. The modification enables such widely disparate procedures as incorporating shortening oil in a cake mix containing flour but no egg, producing a confection or medicated lozenge by dehydrating the dispersion and allowing the melted residue to solidify.

37 Claims, No Drawings

DISPERSED SYSTEMS AND METHOD OF MANUFACTURE

This is a division of application Ser. No. 07/283,742, filed Dec. 13, 1988, now U.S. Pat. No. 5,011,532 which is a continuation-in-part of application Ser. No. 169,838, filed Mar. 18, 1988, now U.S. Pat. No. 4,855,326 which is a continuation-in-part of application Ser. No. 040,371, filed Apr. 20, 1987 now abandoned. A related application is Ser. No. 169,914, filed Mar. 18, 1988 now U.S. Pat. No. 4,873,085.

BACKGROUND OF THE INVENTION

The present invention relates to methods of producing colloidal or colloidal-like dispersions, the products so produced, and to the products used to produce the dispersions. It also relates to methods of diminishing the lack of affinity as between various substances that normally lack affinity for one another. In the prior applications mentioned above, various substances having pharmacological and or cosmetic properties were combined with a sugar and spun into fibers to produce a readily water-soluble product. The various examples enumerated in the prior applications all involved the use of water soluble medicaments and cosmetic substances and were directed to enhancing the solubility rate of the different substances. As an outgrowth of experimentation with a varied catalog of substances it has been discovered that spinning a substance with sugar can alter the medium in which a particular substance can either dissolve or become dispersed, the latter while forming a colloid or colloidal-like dispersion. Whether or not the dispersions to be described herein represent true colloidal dispersions or only pseudo-colloidal dispersions, has yet to be determined. What is evident is that when the spun sugar products to be described herein are added to water, the product disperses autogenously throughout the water and remains dispersed. In most instances one observes a general cloudiness associated with a colloidal suspension. But this is not always the case. Several other novel phenomena have been observed also.

Water and oil normally do not mix. In fact, all oleaginous substances are, in the absence of a surfactant or emulsifier, considered immiscible in water. Also, there are many substances that are soluble in water but considered insoluble in oleaginous materials and lack affinity for such materials. Examples are glycerin and polyethylene glycol. However, one can think of situations where combining such substances might be desirable. For example, combining glycerin with an oil based medicament product in a cough syrup.

SUMMARY OF THE PRESENT INVENTION

It is, therefore, an object of the present invention to provide a a method for rendering a hydrophobic substance dispersable in water without the use of any presently recognized surfactant or emulsifier.

It is another object of the present invention to provide a product containing a normally hydrophobic substance which product is autogenously dispersable in water to form a colloidal or colloidal-like dispersion.

Yet another object of the present invention is to provide a colloidal or colloidal-like dispersion containing water, at least one oleaginous substance and optionally one or more adducts which in their separate state are soluble in water but lack affinity for said oleaginous substances, all without the use of any presently recognized surfactant or emulsifier.

Another object is to enable single or multiple substances to be combined in the presence of water without the need for an emulsifier or surfactant even though such substances normally lack affinity for one another or for the water.

Other objects will occur to those skilled in the subject art after reading the following detailed description.

In accordance with one aspect of the present invention there is provided a mass of spun fibers consisting essentially of one or more sugars where the sugars are capable of being spun into fibers that are readily water-soluble, and an ingredient that in its separate state is hydrophobic, said ingredient being distributed on or incorporated in the fibers of said mass such that said mass of fibers when added to water disperses therein to form a colloidal or colloidal-like dispersion.

In accordance with another aspect of the present invention there is provided a colloidal or colloidal-like dispersion consisting essentially of water, at least one oleaginous substance, at least one sugar that is water-soluble, and optionally one or more adducts which in their separate state are soluble in water but lack affinity for said oleaginous substances.

In accordance with a further aspect of the present invention there is provided a method of rendering a hydrophobic substance dispersable in water which comprises the steps of mixing said substance with a sugar capable of being spun into fibers that are readily water-soluble, and thereafter processing said mixture with a floss producing machine to yield a mass of material that when added to water disperses therein to form a colloidal or colloidal-like dispersion.

In accordance with yet another aspect of the present invention there is provided a method of producing a dispersion which is colloidal or colloidal-like and contains, in addition to water, at least one oleaginous substance, said method comprising the steps of mixing said substance with at least one sugar capable of being spun into fibers that are readily water-soluble, thereafter processing said mixture of substance and sugar using a floss producing machine to yield a mass of product, and introducing said product into a quantity of water thereby producing said dispersion.

The invention will be better understood after reading the following detailed description of the presently preferred embodiments thereof.

DETAILED DESCRIPTION OF THE PRESENTLY PREFERRED EMBODIMENTS

Co-pending application Ser. No. 169,838 describes methods for combining a medicament with any one or more of the water soluble melt spinnable sugars and spinning the combination to produce a readily soluble floss form of the medicament. The disclosure of such application is incorporated herein by reference.

Typical of the discovery that has given rise to the present application is that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. An attempt to measure the size particles in such dispersion has indicated that the particles are usually no greater than about 1.0 micron. The invention can best be described and understood from a consideration of a number of examples.

For the following examples the floss spinning machine used was: Econo floss Model 3017 manufactured by Gold Medal Products Co. of Cincinnati, Ohio. Unless otherwise stated, reference to sucrose in the examples is to "Gold Medal" flossugar, Jolly Berry flavor. Unless otherwise indicated, the temperature of the grid in the spinning machine was about 180° F. (82.2° C.) while the operating speed was about 3800 R.P.M.

EXAMPLE I

A quantity of sucrose was placed in a receptacle along with a quantity of "Bertolli" brand 100% pure olive oil, classico, in the ratio by volume of 4 parts sucrose to 2 parts oil. The material was stirred with a spoon and left to stand for 10 minutes, stirring again after 5 minutes and at the end of the 10 minute interval. The mixture was then spun in the floss spinning machine at the heat setting normally used for the sucrose alone. A luxurious, soft and dense floss, having the odor of olive oil was produced. When a quantity of the floss was placed in a beaker of clear water, the floss appeared to disperse rapidly creating a dispersion that was no longer clear. Left overnight the dispersion appeared unchanged, still uniformly cloudy.

EXAMPLE II

A quantity of unmodified sucrose was spun in the floss spinning machine at the same conditions as in Example I and a quantity of the resultant floss was placed in a beaker with clear water. While the floss disappeared in the water, the water remained perfectly clear, that is, the sugar went into true solution.

EXAMPLE III

The procedure of Example I was repeated substituting for the olive oil a similar quantity of "Johnson & Johnson" Baby Oil. Except for the expected difference in odor, the resultant dispersion in water was the same.

EXAMPLE IV

A quantity of floss produced in Example I was left exposed to the environment in a humid atmosphere for a period of 12 hours with no evidence of deterioration. Floss produced without an oil additive shows evidence of deterioration after a relatively short exposure to a moist atmosphere. It can be understood from this that the oil content serves as a stabilizer for the floss, yet the product disperses readily when added to an aqueous medium.

EXAMPLE V

A quantity of the floss produced in Example I was placed in water in a vessel in the weight ratio of approximately 10% floss to water. The mixture was heated to boiling and removed from the heat. When placed in a clear receptacle the liquid was still cloudy retaining its dispersed condition. The liquid was then placed in a freezer at 20° F. (−6.6° C.) and gradually turned to ice after a prolonged mush stage. The ice remained cloudy. It was then melted in a microwave oven and returned to its original appearance of a colloidal or colloidal-like dispersion.

EXAMPLE VI

The procedure of Example I was repeated with each of the below-listed oleaginous substances with precisely the same results, except that the quantity of sucrose varied between 4 and 5 parts by volume to 2 parts oleaginous substance.

(a) "PEOPLES" pure imported Cod Liver Oil.
(b) "SQUIBB" Mineral Oil.
(c) "NATURE MADE" B-6 complex containing kelp, lecithin and vitamin B-6 with cider vinegar.
(d) "FLEISCHMANS" 100% Corn Oil Margarine.
(e) Lard manufactured by Smithfield Packing Co.

The lard and margarine were first melted in a microwave oven. The B-6 complex, substance (c), was in capsule form and was ground in a coffee grinder and mixed with the sucrose with the addition of a small quantity of water.

EXAMPLE VII

The procedure of Example I was repeated with "Quaker State" 10W-40 Motor Oil, 1 part by volume oil to 3 parts sucrose. The grid temperature of the spinning machine had to be lowered slightly to eliminate mild smoking. The floss appeared silky, heavy and very tough. Actually, the fibers produced by this example appear strong enough to be taken up on a spool.

EXAMPLE VIII

The procedure of Example I was repeated to produce a floss from "CRISCO" 100% Vegetable Oil using 1 part by volume oil to 2.5 parts sucrose. A very silky floss was produced with strong tough fibers. When placed in water a colloidal or colloidal-like dispersion resulted.

EXAMPLE IX

A floss was produced by placing in a bowl ⅛ cup of a Lactose obtained from Sigma chemical Co. of St. Louis, Mo., along with ⅛ cup of "CRISCO" 100% Vegetable Oil. The mixture was stirred with a spoon for 2 minutes and then spun at a grid temperature of approximately 200° F. (93.3° C.). The floss quickly formed a dispersion when added to water.

EXAMPLE X

For this example the materials used were sucrose obtained from Victor Products Co. of Richmond, Va., and polyethylene glycol, m.w. 400, (P-3265) from Sigma Chemical Co. ⅛ cup of sucrose was mixed with ⅛ cup of the polyethylene glycol. The ingredients were stirred for 2 minutes and spun. The resulting floss when added to water is believed to form a dispersion and not a solution. Based upon other experiments described in Examples below it is certain that the polyethylene glycol is modified by the processing with sugar. However, when it is added to water, because of the clarity of the liquid it is difficult to discern a difference from the solution that is formed when pure polyethylene glycol is added to water. With heavy loading the water begins to show some cloudiness.

EXAMPLE XI

Floss produced in Example X was added to a quantity of "CRISCO" 100% Vegetable Oil but would not go into solution or disperse within the oil.

EXAMPLE XII

⅛ cup of the polyethylene glycol floss produced in Example X was added to ⅛ cup of water producing an apparent dispersion. Next, ⅛ cup of the Vegetable Oil floss produced in Example VIII was added to ⅛ cup of water and produced a dispersion. When the two dispersions were mixed a colloidal or colloidal-like dispersion was formed with no evidence of any constituent settling out. Thus, the polyethylene glycol, normally immiscible in oil, was enabled to enter into an intimate dispersion along with the oil.

The unusual behavior and modification of polyethylene glycol and vegetable oil reported in Examples X, XI and XII, does not appear to be limited to those substances. Similar behavior was evidenced with glycerin (glycerol) and is described in the examples that follow.

EXAMPLE XIII

To ⅛ cup of sucrose from Victor Products Co. was added ⅛ cup of glycerin USP distributed by Barre-National Inc. of Baltimore, Md. The mixture was stirred with a spoon in a bowl for three minutes and was then spun into fibers. Mild initial smoking was corrected by slightly lowering the grid temperature. A good textured floss was produced. When ⅛ cup of the floss was placed in water it formed a dispersion similar to that discussed in Example X and not a solution as would be expected from sugar and glycerin individually. Similar to Example XI, the glycerin floss would not mix with pure vegetable oil. Also, pure glycerin does not mix with pure vegetable oil nor does it mix readily with water that already contains glycerin floss.

EXAMPLE XIV

Now, ⅛ cup of the vegetable oil floss produced in Example VIII and ⅛ cup of the glycerin floss produced in Example XIII were placed together in a clear vessel and to this was added ⅛ cup of water. Immediately, the two flosses dispersed in the water to form a colloidal or colloidal-like dispersion.

EXAMPLE XV

To verify the parallel responses, a quantity of vegetable oil floss as produced in Example VIII was added to the glycerin USP but would not mix. Then ⅛ cup of glycerin floss as formed in Example XIII was added to ⅛ cup of pure vegetable oil along with ⅛ cup of water. No mixing or blending occurred.

EXAMPLE XVI

To ⅛ cup of glycerin floss as produced in Example XIII was added a quantity of water and this produced an apparent dispersion. To the dispersion was added a quantity of pure vegetable oil. The oil remained layered. Next, ⅛ cup vegetable oil floss as produced in Example VIII was added to ⅛ cup of water. A dispersion was formed immediately. Thereafter, ⅛ cup of glycerin was added to the dispersion and no blending could be obtained. However, reversing the sequence and mixing the pure glycerin first with water produced a solution (associated with a slight shimmering appearance as the glycerin spreads) in which the vegetable oil floss dispersed when subsequently added.

EXAMPLE XVII

Example XIV was repeated using 1/10 cup each of vegetable oil floss and glycerin floss to which was added ⅛ cup water. Result, immediate dispersion formed having all the appearance of a colloidal dispersion.

EXAMPLE XVIII

1/6 cup of vegetable oil was mixed with ⅛ cup water to which was added 1/10 cup polyethylene glycol. While the polyethylene glycol appeared to enter a dispersed state, the vegetable oil remained separated in globules.

EXAMPLE XIX

Next, 1/10 cup of glycerin floss was added to a mix of 1/6 cup of water and 1/6 cup vegetable oil. The glycerin formed a dispersion but the oil remained in separate globules.

EXAMPLE XX

1/10 cup of mineral oil floss from Example VI was combined in a vessel with 1/10 cup of polyethylene glycol floss from Example X and 1/10 cup of vegetable oil floss from Example IX. To this combination was added ⅛ cup water resulting in an immediate uniform dispersion.

EXAMPLE XXI

To 1/10 cup vegetable oil floss from Example IX was added a previously prepared mixture of 1/10 cup polyethylene glycol and 1/10 cup water resulting in uniform dispersion.

EXAMPLE XXII

To 1/10 cup of vegetable oil floss from Example IX was added a previously prepared mixture of ⅛ cup glycerin USP and ⅛ cup water resulting in uniform dispersion.

EXAMPLE XXIII

In a graduated cylinder was placed 1 oz. of water. Vegetable oil floss prepared in Example VIII was compressed to 30–40 percent of its original as-spun volume, and 2 cups of the compressed floss were added to the water in the cylinder. It dispersed quickly forming a dispersion colloidal in appearance. In like manner 2 cups of similarly compressed mineral oil floss from Example VI, were added to the cylinder, immediately dispersing and forming a quite concentrated dispersion still colloidal in appearance. Finally, 2 cups of similarly compressed polyethylene glycol floss from Example X were added and it too entered the dispersed state. No agitation was used throughout to create the uniform blended dispersion.

Next, the graduated cylinder was placed in a microwave oven and heated on high for about 8 minutes until all evidence of evolving steam disappeared. The resulting dehydrated thick mixture was permitted to cool and formed a solid mass that was slippery to the touch.

Finally, 1 oz. of water was added to the solid product in the graduated cylinder and within 3 minutes a dispersion was observed being formed. After 45 minutes all of the material was back in a dispersed state throughout the water.

The precise explanation for the phenomena implicit in the examples described herein is not known. It is conjectured that the sugar encapsulates minute, possibly molecular, quantities of the oil or other material altering its affinity for water or water containing substances. It has been established that pure water is not required as the dispersion medium as evidenced by the purely arbitrary selection of such mediums, in the following example.

EXAMPLE XXIV

Separate beakers were provided respectively with ⅛ cup of (a) homogenized milk; (b) Diet "Coca Cola"; (c) "Pilsner" Light beer; and (d) water. To each beaker was added ⅛ cup of mineral oil floss from Example VI. In all the beakers the floss quickly entered the dispersed phase.

EXAMPLE XXV

Cocoa butter was mixed with sucrose in the ratio of 1 tablespoon cocoa butter to 2 tablespoons sucrose and spun as in Example I. The resulting fiber was placed in a tub of hot water and immediately dispersed. After bathing in the tub the skin appeared very soft and neither oily not sticky. Apparently, the presence of the oleaginous substance reduces the sticky quality of sucrose.

EXAMPLE XXVI

Cod liver oil, same as in Example VI, was mixed with sucrose, ⅛ cup of each, producing a viscous material. It was spun as in Example I and produced a very rich, heavy and obviously oily floss. A 1 oz. beaker was filled with a quantity of the floss, pressed down firmly. Then ¼ oz. water was added and a thick dispersed system quickly developed.

EXAMPLE XXVII

This example is intended to demonstrate the universality of the phenomenon. First a sugar blend was produced by mixing by volume 40% lactose, 30% maltose and 30% sucrose with sufficient water to dissolve the sugars. The solution was placed in an oven at approximately 120° F. (48.8° C.) for a time sufficient to drive off the water. The residue was allowed to cool for about 2 hours and then broken into crystals for use in the spinning machine.

Using the sugar crystals, 1 teaspoon was mixed with 1 teaspoon of "Caswell Massey" pure lanolin and ⅛ teaspoon oil of violet fragrance. This mix was then spun into floss as in Example I. A nice floss was produced which when added to water produced a dispersion that could be used as a skin toner.

From the foregoing examples it can be concluded that spinning a substance with a sugar or sugars accomplishes a modification of the wettability of the substance with regard to other substances with which the first substance is neither normally miscible or readily dispersable therein. The process can end with the production of spun fibers which can be dispersed in water or a water containing fluid. Alternatively, a dispersion made from the fibers, or at least from material derived from the sugar-spun product, can be dehydrated to produce a solid which enters the dispersed state more readily than the original raw materials prior to treatment. For example, an oil or glycerin based throat medicament can be spun with sucrose or other sugar, form a dispersion with the addition of water, be dehydrated and fused to yield a solid which will have outstanding use as a throat lozenge. The nature of the sugar modified medicament is such that it will coat and line the mucous membranes of the oral cavity much more effectively than heretofore known forms of the medicament. Without the medicament the solid product, plus flavoring agents, becomes a confection.

The affinity developed between an oleaginous substance and water can be used to eliminate need for a surfactant or emulsifier in numerous formulating processes where such was heretofore required. One demonstrable example involves the elimination of the need for eggs in cake mix recipes. To illustrate the concept some examples follow.

EXAMPLE XXVIII

Into a mixing bowl was placed 2 tablespoons of flour. To this was added 4 tablespoons of water and 1 tablespoon of "Crisco" 100% Vegetable Oil. Attempts to mix the oil with the flour and water were unsuccessful until 1 whole egg was added.

EXAMPLE XXIX

Example XXVIII was repeated with the substitution for the pure vegetable oil of vegetable oil floss from Example VIII added in an amount equivalent to 1 tablespoon of the unmodified oil. The floss form of the oil mixed readily with the flour and water, all without the addition of egg.

EXAMPLE XXX

Next, three packaged cake mixes:
(a) "Betty Crocker" Super Moist Devils Food Cake Mix;
(b) "Duncan Hines" Golden Cake Mix; and
(c) "Pillsbury" Plus Yellow Cake Mix
were prepared. No eggs were used even though all directions called for 3 eggs. Each recipe called for oil or margarine, ⅓ cup oil for (a) and (c), ⅓ cup margarine for (b). Example XXIX demonstrated that the oil floss dispersed much better than when egg was used with unmodified oil. Consequently, the equivalent of one half the specified amount of oil or margarine was used when pure oil was replaced by the floss form. The mixes were each placed in a bowl. The mixes (a) and (b) each received a quantity of the vegetable oil floss from Example VIII. The quantity added to mix (a) was the equivalent of 1/6 cup oil, to mix (b) the equivalent of ¼ cup oil. To mix (c) was added ⅓ cup pure oil as called for. No floss was added to mix (c). Next, the specified quantity of water was added to each and the ingredients were mixed with an electric mixer. The mixes (a) and (b) took in the water and other ingredients completely, easily and without separation within the recommended 2 minutes of mixing. However, the (c) mix mixed only with difficulty and only after prolonged blending for at least 6 minutes. All mixes were then baked in an oven following the manufacturer's recommended directions, were removed from the oven, and allowed to cool for 1 hour.

The mixes (a) and (b) produced cakes of excellent texture that were evenly bound with no tendency to crumble. The third mix, mix (c), could not be sliced, crumbled badly, and was obviously not bound. It appeared that the oil and water components had separated during baking.

The foregoing examples demonstrate that a dry mixture can be prepared which disperses readily in an aqueous environment even though one or more of the individual constituents of the mixture normally lack affinity for water or for one another. All that is required is to separately mix each of the normally incompatible constituents with at least one sugar capable of being spun into fibers that are readily water-soluble and then separately spinning the mixtures to produce flosses which are subsequently blended with one another.

While it has been stated above that it cannot be said with certainty that the present invention produces a true colloid, the evidence tends to indicate that the oleaginous substance becomes encapsulated within the sugar, and that the molecules of each become so tightly attached that the sugar does not detach and enter solution when placed in water. Microscopic examination of solid masses produced as in Example XXIII suggests that a solid colloid exists with the oil as the dispersed phase within the sugar as the dispersion medium. In an aqueous environment, the encapsulated molecules become the dispersed phase within the dispersion medium which is aqueous.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A method of rendering a oleaginous substance hydrophilic which comprises the steps of mixing said substance with a sugar capable of being spun into fibers that are readily water-soluble and thereafter spinning said mixture with a floss producing means to yield a mass of hydrophilic fibers.

2. A method of rendering an oleaginous substance dispersable in water which comprises the steps of mixing said substance with a sugar capable of being spun into fibers that are readily water-soluble, and thereafter processing said mixture with a floss producing means to yield a mass of material that when added to water disperses therein to form a colloidal or pseudo-colloidal dispersion.

3. A method according to claim 2, wherein said substance is cod liver oil.

4. A method according to claim 2, wherein said substance is mineral oil.

5. A method according to claim 2, wherein said substance is a composition containing kelp, lecithin, vitamin B6 and cider vinegar.

6. A method according to claim 2, wherein said substance is a corn oil margarine composition.

7. A method according to claim 2, wherein said substance is lard.

8. A method according to claim 2, wherein said substance is vegetable oil.

9. A method according to claim 2, wherein said substance is cocoa butter.

10. A method according to claim 2, wherein said substance is olive oil.

11. A method according to claim 2, wherein said substance is lanolin.

12. A method of producing a dispersion which is colloidal or pseudo-colloidal and contains water, an oleaginous substance, and a material that is soluble in water but lacks affinity for said substance, said method comprising the steps of mixing said material with said water to produce a solution, mixing said substance with a sugar capable of being spun into fibers that are readily water-soluble, thereafter processing said mixture of substance and sugar using a floss producing means to yield a mass of product, and introducing said product into said solution thereby producing said dispersion.

13. A method according to claim 12, wherein said material is glycerin.

14. A method according to claim 13, wherein said oleaginous substance is selected from the group consisting of cod liver oil, mineral oil, vegetable oil, lard, cocoa butter, lanolin, and combinations thereof.

15. A method according to claim 12, wherein said material is polyethylene glycol.

16. A method according to claim 15, wherein said oleaginous substance is selected from the group consisting of cod liver oil, mineral oil, vegetable oil, lard, cocoa butter, lanolin, and combinations thereof.

17. A colloidal or pseudo-colloidal dispersion consisting essentially of water, at least one oleaginous substance, at least one sugar that is water-soluble, and optionally one or more adducts which in their separate state are soluble in water but lack affinity for said oleaginous substances.

18. A colloidal or pseudo-colloidal dispersion according to claim 17, wherein said oleaginous substances are selected from the group consisting of, cod liver oil, mineral oil, vegetable oil, lard, cocoa butter, lanolin, and combinations thereof.

19. A colloidal or pseudo-colloidal dispersion according to claim 18, wherein said adducts are selected from the group consisting of glycerin and polyethylene glycol.

20. A colloidal or pseudo-colloidal dispersion according to claim 17, wherein said adducts are selected from the group consisting of glycerin and polyethylene glycol.

21. A method of producing a dispersion which is colloidal or pseudo-colloidal and contains water, an oleaginous substance, and a material that is soluble in water but lacks affinity for said substance, said method comprising the steps of separately mixing said substance and said material each with at least one sugar capable of being spun into fibers that are readily water-soluble, thereafter separately spinning said mixtures of substance and sugar and material and sugar, using a floss producing means to yield respective masses of product, and introducing said products into a quantity of water thereby producing said dispersion.

22. A method according to claim 21, wherein said material is glycerin.

23. A method according to claim 22, wherein said oleaginous substance is selected from the group consisting of cod liver oil, mineral oil, vegetable oil, lard, cocoa butter, lanolin, and combinations thereof.

24. A method according to claim 21, wherein said material is polyethylene glycol.

25. A method according to claim 24, wherein said oleaginous substance is selected from the group consisting of cod liver oil, mineral oil, vegetable oil, lard, cocoa butter, lanolin, and combinations thereof.

26. A method of producing a dispersion which is colloidal or pseudo-colloidal and contains, in addition to water, at least one oleaginous substance, said method comprising the steps of mixing said substance with at least one sugar capable of being spun into fibers that are readily water-soluble, thereafter processing said mixture of substance and sugar using a floss producing means to yield a mass of product, and introducing said product into a quantity of water thereby producing said dispersion.

27. A method according to claim 26, wherein said oleaginous substance is selected from the group consisting of cod liver oil, mineral oil, vegetable oil, lard, cocoa butter, lanolin, and combinations thereof.

28. A cake mix preparation including flour, at least one oleaginous substance, at least one sugar that is water-soluble, and one or more adducts that have affinity for water, where use of the mix requires blending with water or a water containing liquid, characterized in that said oleaginous substance and said sugar have been subjected to a blending and melt-spinning step rendering said oleaginous substance dispersable in water without the intervention of a separate surfactant.

29. A method of producing a solid body of a material that is autogenously dispersable in water or a water-containing medium which method comprises the steps of mixing an oleaginous substance with at least one sugar and optionally one or more adducts which are soluble in water but lack affinity for said oleaginous substance to produce a blend, thereafter spinning said blend using a floss producing means to yield a mass of fibrous product, combining said fibrous product with sufficient water to create a dispersion with said product in a dispersed state within said water, applying to said dispersion heat at a sufficient level and for a sufficient time to eliminate at least the major portions of said water from said dispersion and to melt the residue, thereafter enabling said residue to cool and solidify thereby forming said body.

30. A lozenge produced by the method of claim 29.

31. A confection produced by the method of claim 29.

32. A method of stabilizing spun sugar which comprises in combination the steps of combining a quantity of an oleaginous substance with at least one sugar capable of being spun into fibers that are readily water-soluble and thereafter processing said substance and sugar using a floss producing means to yield a mass of span fibers.

33. A method of producing a dry mixture which disperses readily in an aqueous environment although one or more of the individual constituents of said mixture normally lack affinity for water or for one another, and at least one of said constituents is an oleaginous substance, said method comprising the steps of separately mixing with each of said one or more constituents, at least one sugar capable of being spun into fibers that are readily water-soluble, thereafter separately processing said mixtures of sugar and constituent using a floss producing means to yield respective masses of product, and mixing together said products to produce a dry mix that readily mixes with an aqueous medium.

34. A method according to claim 33, wherein said oleaginous substance is selected from the group consisting of cod liver oil, mineral oil, vegetable oil, lard, cocoa butter, lanolin, and combinations thereof.

35. A method according to claim 34, wherein at least one of said constituents lacks affinity for an oleaginous medium.

36. A method according to claim 33, wherein at least one of said constituents lacks affinity for an oleaginous medium.

37. A method according to claim 33, wherein at least one of said constituents is a glycerol.

* * * * *